United States Patent [19]

Gilbert

[11] Patent Number: 4,476,060

[45] Date of Patent: Oct. 9, 1984

[54] 1,3,5,7-TETRANITROXYADAMANTANE

[75] Inventor: Everett E. Gilbert, Morristown, N.J.

[73] Assignee: The United States of America as represented by the Secretary of the Army, Washington, D.C.

[21] Appl. No.: 535,481

[22] Filed: Sep. 26, 1983

[51] Int. Cl.$^3$ .............................................. C07C 77/00
[52] U.S. Cl. ...................................... 260/466; 149/88
[58] Field of Search ........................... 149/88; 260/466; 568/941

[56] References Cited

U.S. PATENT DOCUMENTS 4,329,522 5/1982 Gilbert et al. ........................ 568/941

OTHER PUBLICATIONS

Friedman et al., Chem. Abs., vol. 85, 46054d, 1976.

Primary Examiner—Leland A. Sebastian
Attorney, Agent, or Firm—Anthony T. Lane; Robert P. Gibson; Harold H. Card, Jr.

[57] ABSTRACT 1,3,5,7-Tetranitroxyadamantane is a novel propellant having desirably low impact sensitivity. It can be prepared by reacting 1,3,5,7-tetrahydroxyadamantane or 1,3,5,7-tetraacetoxyadamantane with mixed conc. nitric and sulfuric acids.

4 Claims, No Drawings

1,3,5,7-TETRANITROXYADAMANTANE

GOVERNMENT RIGHTS

The invention described herein may be manufactured, used and licensed by the Government for Government purposes without the payment to me of any royalties thereon.

BACKGROUND OF THE INVENTION

U.S. Pat. No. 4,329,522, E. E. Gilbert and G. P. Sollot inventors, is directed to the novel explosive compound 1,3,5,7-Tetranitroadamantane. The compound is a high explosive, which possesses excellent thermal and impact stability.

The present invention relates to a somewhat molecularly analogous compound, which can be employed as a propellant having low impact sensitivity.

SUMMARY AND DETAILED DESCRIPTION OF THE INVENTION

The present invention provides a novel compound 1,3,5,7-tetranitroxyadamantane and a method for producing same. The novel compound contains four more oxygen atoms than 1,3,5,7-tetranitroadamantane, and can be used as a propellant alone or in mixture with other compounds in gas-producing pyrotechnic compositions. The novel compound can be obtained by reacting 1,3,5,7-tetrahydroxy- or 1,3,5,7-tetraacetoxyadamantane with a nitrating agent such as conc. nitric acid alone or in mixture with conc. sulfuric acid, advantageously in the presence of an inert, water-immiscible organic solvent.

The following example illustrates a method for preparing the novel compound of the present invention.

EXAMPLE 1,3,5,7-Tetrahydroxyadamantane (1.5 g, 0.0015 mole) prepared by the method of Stetter and Krause (Ann. 717, 60-63 (1968) was added to conc. 96% sulfuric acid (10.0 ml) in a glass reaction flask at 0° C. with agitation. Methylene chloride (50 ml) was added to the mixture, which was then cooled to −10° C. Conc. 90% nitric acid (8.0 ml=0.19 mol) was next added dropwise with stirring, after which the mixture was agitated for 30 minutes while warming to 0° C. Ice was then added and the methylene chloride layer was separated, dried and evaporated to dryness, yielding 1.4 g of 1,3,5,7-tetranitroxyadamantane, corresponding to 64% of theory yield. It had a melting point of 138°-9° C. when recrystallized from n-butanol. Analysis (MIL-STD-108.1.3)-calculated 65.3% $NO_3$; found 63.8. The infrared spectrum showed strong peaks at 1630, 1280 and 865 $cm^{-1}$, corresponding to $-ONO_2$. NMR ($d_6$-acetone)δ2.90(s), which agrees with the assigned structure.

When the foregoing procedure was repeated but using an equivalent amount of 1,3,5,7-tetracetoxyadamantane (prepared as described by Stetter and Krause, loc. cit.) in place of 1,3,5,7-tetrahydroxyadamantane, the yield of 1,3,5,7-tetranitroxyadamantane obtained was 63% of theory.

The novel compound was tested as follows:

Shock Sensitivity. The exploding foil test employed is described in an article entitled "Exploding Foil Shock Sensitivity Test" by W. E. Voreck and R. W. Velicky, published in the Proceedings of the International Symposium on Detonation (7th) held at Annapolis, MD, on June 16-19, 1981 (Available from the Naval Surface Weapons Center, Attn: E421 White Oak, Silver Springs, MD 20910, Report Number NSWC/WP-82-334, pages 475-479). The test results set forth in the following table show that the novel compound possesses a desirably low degree of shock sensitivity.

| Compound | Voltage (KV) | % Fired | Critical Energy ($Cal/CM^2$) |
|---|---|---|---|
| 1,3,5,7-tetranitroxyadamantane | 14 | 50 | 42 |
| TNT (2,4,6-trinitrotoluene) | 10.8 | 50 | 34 |
| RDX (1,3,5-trinitro-1,3,5-triazacyclohexane) | 4.8 | 50 | 11 |

Thermogravimetric Analysis. The novel compound when heated above its melting point, underwent rapid, exothermic gas evolution which began at 153° C. and levelled off at 185° C., at which point the sample had lost 83% of its original weight. It is noteworthy that 1,3,5,7-tetranitroadamantane by contrast melts with charring at 361° C.

Ignition Test. Crystals of 1,3,5,7-tetranitroxyadamantane, when heated on a spatula over a Bunsen flame, melted and flashed shortly thereafter.

The foregoing data indicate that 1,3,5,7-tetranitroxyadamantane is suitable for use as a propellant. It is also useful in fire control systems, such as automatic sprinklers, where pressure is generated by the application of external heat.

I claim:

1. 1,3,5,7-Tetranitroxyadamantane.

2. A process for preparing 1,3,5,7-tetranitroxyadamantane which comprises reacting 1,3,5,7-tetrahydroxyadamantane or 1,3,5,7-tetracetoxyadamantane with a nitrating agent.

3. The process of claim 2, wherein the nitrating agent is a mixture of nitric acid and sulfuric acid.

4. The process of claim 3, wherein the adamantane reactant is 1,3,5,7-tetrahydroxyadamantane.

* * * * *